United States Patent
Elhawary et al.

(10) Patent No.: US 9,750,575 B2
(45) Date of Patent: Sep. 5, 2017

(54) EVALUATION OF PATENCY USING PHOTO-PLETHYSMOGRAPHY ON ENDOSCOPE IMAGES

(71) Applicant: KONINKLIJKE PHILIPS N.V., Eindhoven (NL)

(72) Inventors: Haytham Elhawary, New York, NY (US); Aleksandra Popovic, New York, NY (US); Willem Verkruijsse, Veldoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 78 days.

(21) Appl. No.: 14/407,972

(22) PCT Filed: Jun. 20, 2013

(86) PCT No.: PCT/IB2013/055071
§ 371 (c)(1),
(2) Date: Dec. 15, 2014

(87) PCT Pub. No.: WO2014/001981
PCT Pub. Date: Jan. 3, 2014

(65) Prior Publication Data
US 2015/0164592 A1 Jun. 18, 2015

Related U.S. Application Data

(60) Provisional application No. 61/665,335, filed on Jun. 28, 2012.

(51) Int. Cl.
*A61B 5/00* (2006.01)
*A61B 19/00* (2006.01)
(Continued)

(52) U.S. Cl.
CPC ........ *A61B 19/2203* (2013.01); *A61B 1/0005* (2013.01); *A61B 5/0084* (2013.01);
(Continued)

(58) Field of Classification Search
CPC .. A61B 5/05; A61B 5/06; A61B 5/065; A61B 5/066; A61B 5/062; A61B 5/08
See application file for complete search history.

(56) References Cited

U.S. PATENT DOCUMENTS

| 7,881,777 | B2 | 2/2011 | Docherty |
| 2005/0182295 | A1* | 8/2005 | Soper ............... A61B 1/0008 600/117 |
| 2010/0160798 | A1* | 6/2010 | Banet ............... A61B 5/02125 600/490 |

FOREIGN PATENT DOCUMENTS

| DE | 19741982 A1 | 10/1998 |
| WO | 2012035492 A1 | 3/2012 |
| WO | 2012046182 A1 | 4/2012 |

OTHER PUBLICATIONS

Hulsbusch: "Ein bildgestutztes, funktionelles Verfahren zur optpelektronischen Erfassung der Hautperfusion", Dissertation Technischen Hochschule Aachen, Jan. 28, 2008, pp. 1-145. XP007913039.

(Continued)

*Primary Examiner* — Joel Lamprecht

(57) ABSTRACT

A system for evaluating patency includes a light sensor (128) positionable relative to a blood vessel to receive light from the blood vessel and convert the light into an image signal. A photo-plethysmography (PPG) interpretation module (115) is configured to receive the image signal and output pixel values in an image representing PPG information. An image generation module (148) is coupled to the PPG interpretation module to receive the pixel values and generate a PPG map to be output to a display for analysis.

15 Claims, 6 Drawing Sheets

(51) Int. Cl.
*A61B 5/0295* (2006.01)
*A61B 1/00* (2006.01)
*A61B 5/06* (2006.01)
*A61B 5/026* (2006.01)
*A61B 5/1459* (2006.01)
*A61B 34/30* (2016.01)

(52) U.S. Cl.
CPC .......... *A61B 5/0261* (2013.01); *A61B 5/0295* (2013.01); *A61B 5/061* (2013.01); *A61B 5/1459* (2013.01); *A61B 5/4851* (2013.01); *A61B 34/30* (2016.02); *A61B 5/7285* (2013.01); *A61B 2034/301* (2016.02)

(56) References Cited

OTHER PUBLICATIONS

Wim Verkruysse et al, "Remote plethysmographic imaging using ambient light", Optics Express, vol. 16, No. 26, Dec. 22, 2008, p. 21434, XP055065281, ISSN: 1094-4087, DOI: 10.1364/0E.16.021434.

Kirk H. Shelley et al, "The Use of Joint Time Frequency Analysis to Quantify the effect of Ventilation on the Pulse Oximeter Waveforn", Journal of Clinical Monitoring and Computing (2006) 20: 81-87, DOI: 10.1007/s10877-006-9010-7.

* cited by examiner

EVALUATION OF PATENCY USING PHOTO-PLETHYSMOGRAPHY ON ENDOSCOPE IMAGES

CROSS-REFERENCE TO PRIOR APPLICATIONS

This application is the U.S. National Phase application under 35 U.S.C. §371 of International Application No. PCT/IB2013/055071, filed on Jun. 20, 2013, which claims the benefit of U.S. Provisional Patent Application No. 61/665,335, filed on Jun. 28, 2012. These applications are hereby incorporated by reference herein.

This disclosure relates to medical instruments and procedures and more particularly to monitoring fluid flow in tissue using photo-plethysmography (PPG) information.

During cardiac bypass surgery, a surgeon uses one or more vessels from the body to bypass an atherosclerotic narrowing in coronary arteries. This is performed with the intention to increase blood flow in the coronary arteries, which supply blood to myocardial tissue of the heart. During minimally invasive (MI) cardiac bypass surgery, elongated instruments are inserted into small incisions in the chest of a patient, and an endoscope provides visualization. In robotic guided MI cardiac bypass surgery, one or more of the instruments (or endoscope) are controlled by a robotic device. Cardiac bypass surgery can be performed with the patient using cardiopulmonary bypass and the heart in cardiac arrest, or with the heart beating.

Graft patency after bypass is validated using X-ray angiography or Ultrasound intraoperatively or using volumetric imaging (computed tomography (CT), magnetic resonance imaging (MRI)) postoperatively. Both intraoperative techniques validate the flow in the graft and in coronary arteries downstream from the graft. However, a successful revascularization of arteries may not necessarily lead to a successful perfusion in the heart muscle, since the flow in smaller vessels, which are not visible in conventional imaging, may also be obstructed. Additionally, these imaging modalities are often not available to surgeons.

In accordance with an exemplary embodiment of the present invention, a system for evaluating patency is described that includes a light sensor positionable relative to a vessel to plethysmography (PPG) interpretation module is configured to receive the image signal and output pixel values in an image representing PPG information. An image generation module is coupled to the PPG interpretation module to receive the pixel values and generate a PPG map to be output to a display for analysis.

For example, the light sensor can include a camera mounted on an endoscope and/or over an open incision to permit light to reach the camera from the blood vessel. The light sensor positionable relative to the blood vessel can be positioned using a robot. The light sensor can be positionable relative to the blood vessel at a first time and positioned in a same position at a second time such that PPG signals can be compared to determine PPG changes in the blood vessel. The system can further include a robot configured to permit repeatable positioning of the light sensor at different times. It is also possible that the image generation module can generate a subtraction image of the PPG signals at different times. The subtraction image can be overlaid on an image collected by the light sensor. It is also possible that the PPG map can be overlaid on an image, such as, e.g., an X-ray image, collected by the light sensor. Further, the blood vessel can include a bypass graft and the PPG map can indicate blood flow through the graft at different times.

In accordance with another exemplary embodiment of the present invention, a system for evaluating patency is described that includes an endoscope including a camera, the endoscope being positionable inside a body relative to a blood vessel to receive light from the blood vessel and convert the light into an image signal. A photo-plethysmography (PPG) interpretation module can be configured to receive the image signal, decipher PPG information from the image signal and output pixel values in an image representing PPG information. An image generation module can be coupled to the PPG interpretation module to receive the pixel values and generate PPG maps corresponding to a plurality of times. A such that differences in the PPG maps represent differences in blood flow through the blood vessel.

For example, the blood vessel can include a bypass graft and the endoscope can be positionable in a same position before and after revascularization to permit a comparison of blood flow using the PPG maps. The system can further include a robot configured to permit repeatable positioning of the endoscope at different times. It is also possible that the image generation module can generate a subtraction image of the PPG information at different times. The subtraction image can be overlaid on an image collected by the camera. The PPG maps can be overlaid on an image, such as, e.g., an X-ray image, collected by the camera. Further, the blood vessel can include a bypass graft and the PPG maps can indicate blood flow through the graft at different times.

In accordance with yet another exemplary embodiment of the present invention, a method for evaluating patency is described that includes positioning a light sensor relative to a blood vessel to receive light from the blood vessel; converting the light into an image signal; interpreting the image signal to determine a photo-plethysmography (PPG) signal and output pixel values in an image representing PPG information; generating a PPG map to be output to a display for analysis from the pixel values; and analyzing at least one PPG map to determine patency of the blood vessel.

For example, the light sensor can include a camera mounted on an endoscope and/or over an open incision. Positioning the light sensor can include positioning the light sensor at a same position at different times such that PPG signals can be compared to determine PPG changes in the blood vessel. It is also possible that positioning the light sensor can include employing a robot to permit repeatable positioning of the light sensor at different times. The method can further include generating a subtraction image from PPG maps at different times. by the light sensor. It is also possible that the blood vessel includes a bypass graft and the PPG map indicates blood flow through the graft at different times. The method can further include accounting for motion in the blood vessel to register PPG maps. The accounting can include providing a grid overlaid on the image signal of the blood vessel, where each portion of the grid includes a tracked point to follow to determine the motion of the blood vessel, for example. It is also possible that the accounting includes providing an electro-cardiogram (ECG) signal, and triggering a PPG measurement at corresponding positions along the ECG graph to account for motion of the blood vessel.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
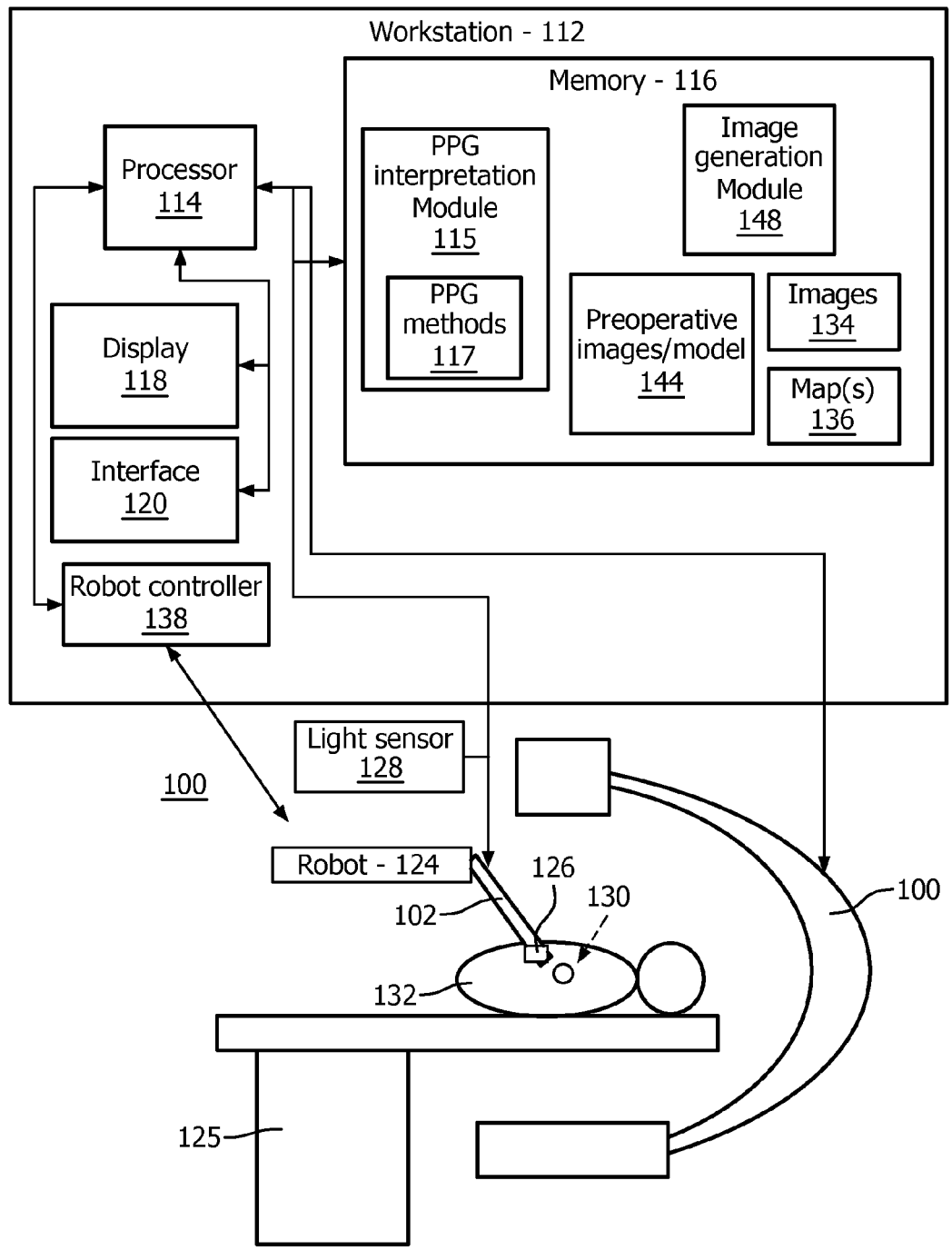
FIG. 1 is a block/flow diagram showing a system for determining photo-plethysmography (PPG) signals for tissue patency in accordance with one embodiment.

In accordance with the present principles, system and methods are provided that determine fluid flow in a region of interest using light emitted or reflected from tissue. In one embodiment, photo-plethysmography (PPG) is employed to evaluate blood flow in tissue. PPG uses light reflectance or transmission to detect cardio-vascular pulse waves travelling through the body. PPG is based on the principle that blood absorbs light more than the surrounding tissue so variations in blood volume affect transmission or reflectance accordingly. PPG signals may be employed to detect respiration and heart rate using only a CCD camera and ambient light illumination. The systems and methods described herein may extract, e.g., green and blue color pixel intensities from regions of interest on the CCD camera based image, and then measure their variation over time. Other information may be extracted and monitored as well. Higher amplitude signals correspond to a higher reflectance and thus a smaller blood volume at the location of the imaged pixels. PPG maps can be generated by plotting a PPG signal at each pixel. The use of PPG enables the extraction of information about heart and respiration rate from a video. The intensity of the signal or pixel on a PPG map is proportional to blood volume, at different phases during the heart beat cycle.

PPG may be employed to extract vital signs from subjects in a completely non-invasive and inexpensive way, using regular CCD-based cameras. Vital signs that can be measured with this technique (PPG) include heart rate, heart rate variability, respiration rate, arterial oxygen saturation (SpO2). PPG may also provide valuable physiological information, e.g., a shape of the plethysmographic waveform and the spatial distribution (across anatomical locations) of the PPG signals (i.e., PPG imaging) can be provided. during surgery changes the modulation depth of respiration on the PPG signal.

In one embodiment, the present principles provide a measure for the validation of the success of a bypass procedure using endoscope images of the heart and PPG, in which blood flow and volume can be compared directly before and after the bypass has been performed using the PPG signals, and a visualization method for the surgeon to evaluate blood volume in the myocardial tissue and vessels. PPG map variations before and after bypass, after processing endoscope images, can show the increased blood volume indicative of a successful revascularization. The present principles may be employed to check graft patency using PPG signals, e.g., in the case of beating heart surgery, using feature tracking. A method to check graft patency using PPG signals in the case of beating heart surgery using gating with ECG signals may also be employed. In another embodiment, a method to combine PPG images and X-ray images for a comprehensive validation framework is disclosed.

It should be understood that the present invention will be described in terms of medical instruments and procedures; however, the teachings of the present invention are much broader and are applicable to any structure or system where flow measurements can be made using light collected from a surface. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for photo-plethysmography (PPG) reading and analysis is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a PPG interpretation module 115 configured to analyze light reflectance or transmission to detect pulse waves travelling through tissue. In a particularly useful embodiment, cardio-vascular or pulmonary systems are analyzed using light transmittance and/or reflectance. Since blood absorbs light more than the surrounding tissue, variations in blood volume are correlated to the transmission or reflectance of light from tissue. The interpretation module 115 is configured to interpret optical signals from a light capturing device or sensor 128, such as a camera (e.g., a CCD camera) or optical waveguide and an imaging device (e.g., light/photo sensors), etc. The optical signals are preferably converted to digital images with pixel values. The interpretation module 115 includes PPG pulse and wave methods 117 configured to decipher small changes in reflectance or transmittance, which may be rendered as pixel intensity/color variations on a display or image (e.g., a PPG map). The methods may include Fast Fourier Transforms and other mathematical algorithms adapted to output PPG signal differences to mounted on or in a medical device 102. The medical device 102 may include a catheter, a guidewire, a probe, an endoscope, a robot, an electrode, a filter device, a balloon device, or other medical component, etc.

In one embodiment, workstation 112 includes an image generation module 148 configured to receive feedback from the interpretation module 115 to display an image of pixel data (e.g., variation of color components or intensities of color components, e.g., blue and green) collected from the images through the light capturing device 128. In one embodiment, the colored pixel data includes pixel intensity. The image generation module 148 may output, e.g., blue and green pixel data accumulated over time to generate a graph or graphs. The graph or graphs may be displayed on a display 118 to provide a reading or information on blood flow through tissue. The image generation module 148 may be employed to generate grids or other overlaid information in images. For example, the grids may be employed to track many points in the image to account for movement in the image over time (described below with respect to FIG. 4). The image generation module 148 may be configured to enhance the images and provide comparison tools for comparing PPG maps (before and after images) to evaluate blood flow through a blood vessel.

In particularly useful embodiments, internal tissue 130 of a body 132 (illustratively depicted on an operating table 125) is analyzed in accordance with the present principles. In one embodiment, the internal tissue 130 includes a coronary graft during or after bypass surgery. The internal tissue 130 is accessed for photo imaging using an endoscope 102 with the light capturing device 128. An image or images 134 of the internal tissue 130 is/are collected over time and recorded from the light sensor 128 or camera. The endoscope 102 includes a light or lights 126 configured to illuminate the tissue 130. The light or lights 126 may produce light at particular wavelengths (e.g., red or infrared, although other measurement. It should be understood that the heat or other electromagnetic signature may be employed without light or other radiation source. The PPG signals may be generated from data collected from multiple channels (e.g., more than one sensor).

Images 134 are collected and interpreted by the interpretation module 115 to determine pixel values of interest. Once the pixel values are determined, the pixel values are output to the image generation module 148 to be displayed on the display device 118. Workstation 112 includes the display 118 for viewing internal images of a subject (patient) or tissue 130. Internal images 144 may include preoperative or intraoperative images of the body 132. These images may be collected by another imaging modality or system 110. PPG maps 136 may be overlaid on images 134 and/or 144. The image generation module 148 may overlay the data on the image 134 to create an overlay, map 136 or other rendering of the collected data. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

A comparison of maps 136 at different times provides a preferable mode of operation for determining patency. The position of the light sensing device 128 (in the endoscope 102 for internal applications) is maintained or returned to a same position at two different times (e.g., before and after a graft has been installed). In one embodiment, the same position is manually achieved. In another embodiment, a robot 124 is controlled by a robot controller 138 to return to the same before and after position. In yet another embodiment, PPG light measurements are timed by movement cycles (e.g., heartbeat, or breathing cycles). In this way, the measurements are made at the same time/position of the anatomy to account for cycle measurements, etc.

The PPG principle is employed to ensure that the bypass has been successful during the interventional procedure. Since the endoscope 102 may include a camera (e.g., light collecting device 128) during the minimally invasive procedure, the images 134 from the camera can be used to extract information about the blood flow and volume before and after the bypass has been performed. This imaging can be used adjuvant to other imaging by, e.g., imaging device 110 or as a stand-alone imaging modality even in operating rooms not equipped with X-ray devices. Imaging device 110 is illustratively depicted as a C-arm X-ray system; however, other imaging modes may be employed instead or in addition to X-rays.

Advantageously, evaluating graft patency using only endoscope images without any additional hardware may be provided. Images for graft patency evaluation are subjected to PPG algorithms/methods 117 in module 115 to output PPG maps 136. While the present example describes graft patency, the present principles are applicable to not only coronary artery bypass grafting but to any other surgical procedure where revascularization is performed or blood flow needs to be evaluated. In addition, any procedure where changes in blood volume and flow are expected as a result can be validated using the present principles, for example, tumor ablation, focused ultrasound ablation, etc.

In the example, blood flow and volume can be compared directly before and after the bypass has been performed using PPG signals. This can be employed to check graft patency using the PPG signals in the case of beating heart surgery by also employing feature tracking in the image of the heart or blood vessel. The graft patency can also be checked using the PPG signals in the case of beating heart surgery using gating with ECG signals.

Feature tracking may include comparing two or more PPG signals over time; the signals are extracted from the same anatomical position each time. A salient or distinctive motion of the tissue. One way on doing this is to divide the image into a grid and track points in each of the cells of the grid to ensure that PPG signals are extracted from the same set of anatomical points at two different time points. This can also be achieved by other tracking methods.

Imaging device 110 may include a fluoroscopy (X-ray) imaging system, a computed tomography (CT) system, a magnetic resonance imaging (MRI) system, and Ultrasonic (US) system, etc. In an open surgery, a small CCD camera (e.g., externally mounted camera) can be located above a surgical field to perform similar analysis to the internal procedures performed with, e.g., a camera on an endoscope.

Figure 2:
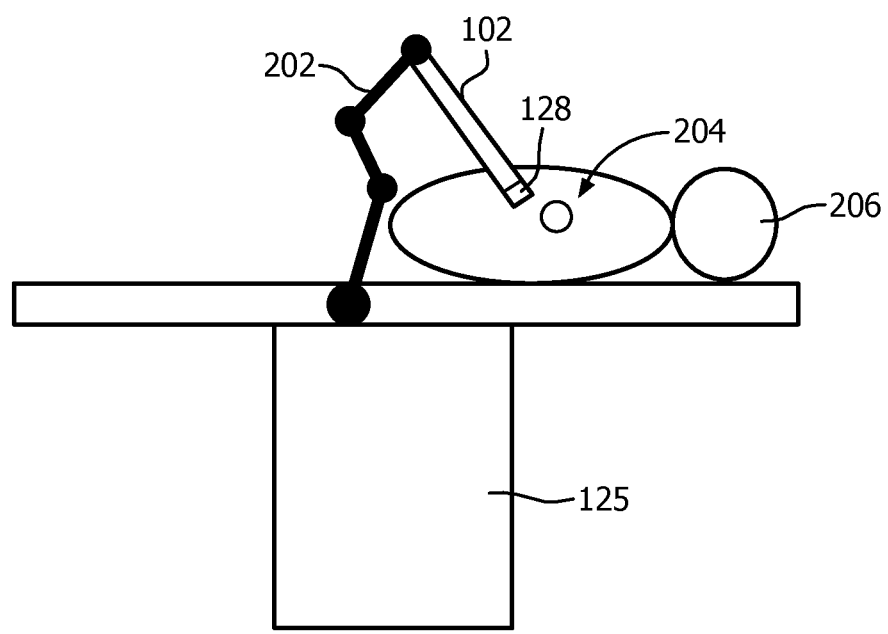
FIG. 2 is a diagram showing another system set-up for determining PPG signals using a robot guided endoscope for blood vessel patency in accordance with another embodiment.

Referring to FIG. 2, another illustrative set-up is shown including a robot 202 controlled by the workstation 112 (FIG. 1). A surgeon proceeds to perform a minimally invasive cardiac bypass surgery in the standard way. Before the bypass and the anastomosis are performed, the endoscope 102 with the camera 128 is located above a heart 204 in a patient 206. Imaging takes place preferably close to an area where the bypass will be performed, that is, the location on the coronary artery with the atherosclerotic narrowing. If this target anatomy cannot be seen, then an overlay fusing pre-operative images (e.g., CT scans) and endoscope images can be performed.

If the robot 202 is used to guide the endoscope 102, joint positions of the robot 202 when the endoscope 102 is positioned correctly over the heart 204 can be stored, to be referred to later after the bypass has been completed so that the position can be reproduced for imaging the heart 204. With the endoscope 102 in place, endoscope images can be taken over a period of time and PPG maps can then be generated for each image.

Once the bypass has been completed, the endoscope 102 is located in a same position as before the bypass. In the case of the robot guided endoscopy, the robot 202 can return to maps are generated again. The PPG signals before and after the bypass should show a strong difference, given that the vessels downstream from the bypass location, as well as the myocardial tissue should be receiving higher quantities of blood from the bypassed vessel. If this were not the case, then the signals would be very similar.

For the surgeon, visualization of the PPG maps can be presented in several ways to facilitate the evaluation. The before and after PPG maps can be shown side by side, as well with a subtraction image. These images and maps may be generated by the image generation module 148 (FIG. 1). The subtraction image can be color mapped to show the locations with the largest difference in signal, indicating the tissue where blood flow has changed the most. In addition, the color maps can be overlaid onto the endoscope images to give a better sense of where the highest difference in blood volume can be found. Other useful information may also be gleaned from the maps.

Figure 3:
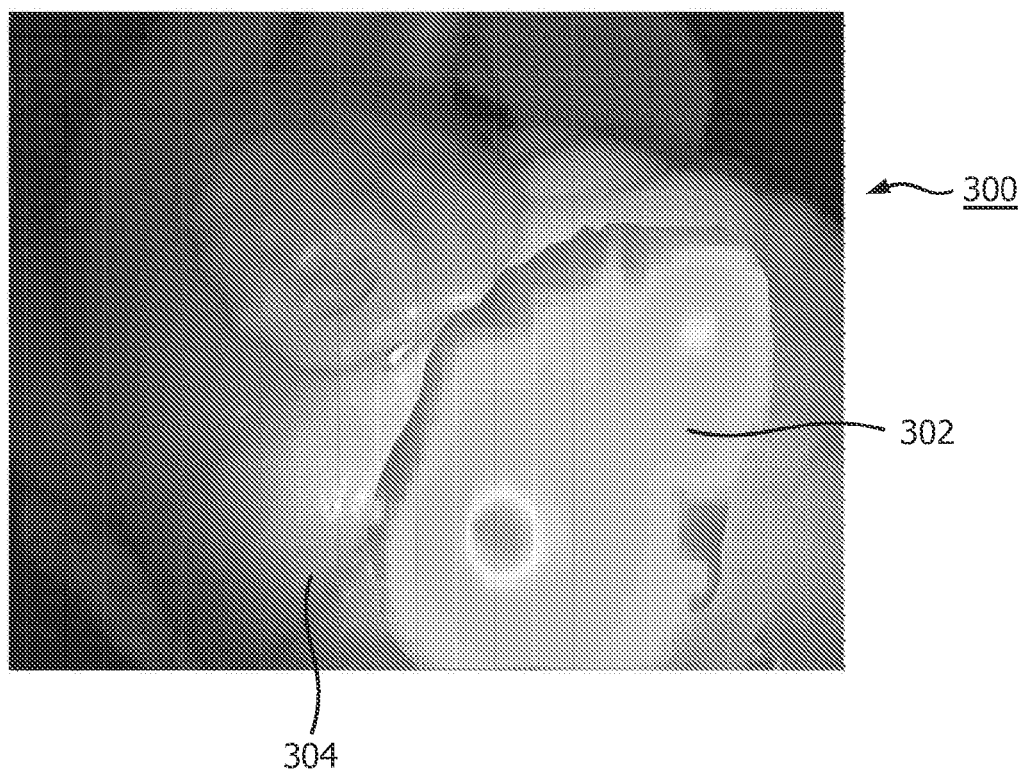
FIG. 3 is an endoscopic image showing a heart with a subtraction image of PPG maps overlaid thereon in accordance with another embodiment.

Referring to FIG. 3, an illustrative image 300 is shown having a color map 302 overlaid onto an endoscope image 304 of a heart 306. The color map 302 provides PPG subtraction signals between myocardial tissue before and after a bypass procedure (e.g., before pixel value subtracted from the after pixel value (or vice versa) to generate a difference or subtraction map). In this case, the higher the signal intensity on the color map 302 indicates a larger difference in blood volume between the pre- and post-bypass images. If large differences are not observed downstream from the bypass location, then success of the procedure is questionable and further investigation is needed.

Figure 4:
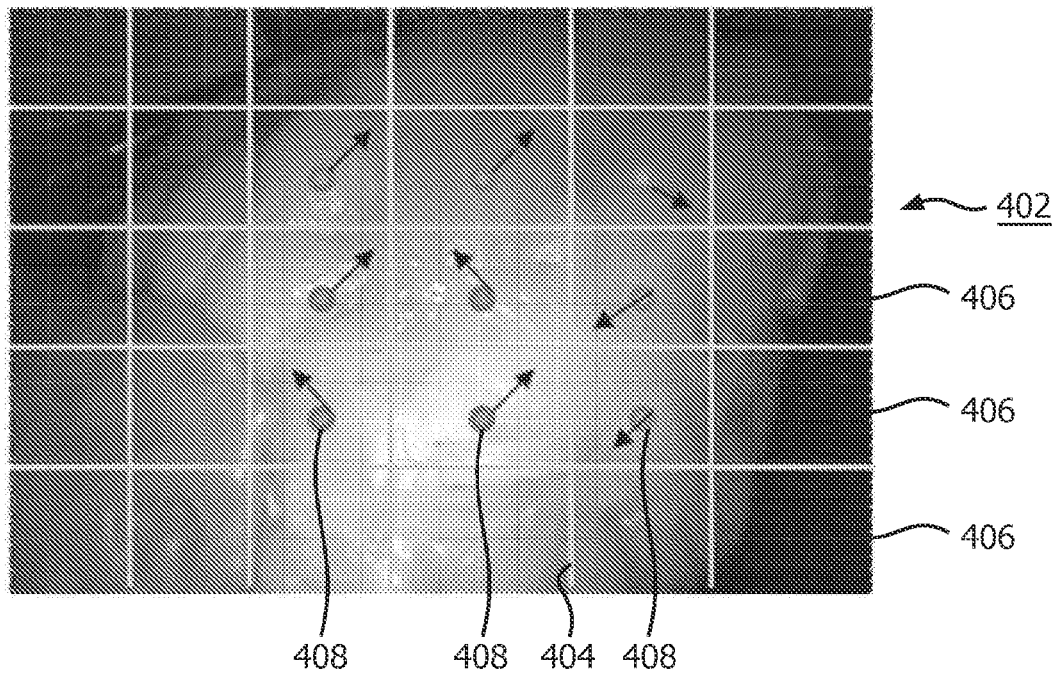
FIG. 4 is an endoscopic image showing a heart with a grid image overlaid thereon to evaluate point movements in accordance with another embodiment.

PPG signals are very sensitive to motion. If certain pixels move in the image, then the PPG signal will be very different and may not correspond to the expected values. In the case where the patient is not on a cardiopulmonary bypass machine, the beating heart may cause sufficient motion to render the PPG signal useless. FIG. 4 describes an embodiment Referring to FIG. 4, an image 402 is shown having a grid 404 dividing the image 402 into portions 406. Each portion 406 includes at least one point 408 which is tracked in each grid portion 406. PPG signals can be obtained at each grid location or portion 406. The tracked point 408 (e.g., a center point of each grid, although other points may be employed) can be tracked in real-time in the image by viewing and comparing images sequence. This would permit PPG signals to be comparable over time as the maps can be registered to the tracked point. While dividing the image 402 into the grid 404 and tracking points 408 in each of the cells 406 is one effective method to ensure that PPG signals are extracted from the same set of anatomical points at two different time points, other tracking methods may be employed and are contemplated, e.g., tracking salient features on the image rather than center points, etc.

Figure 5:
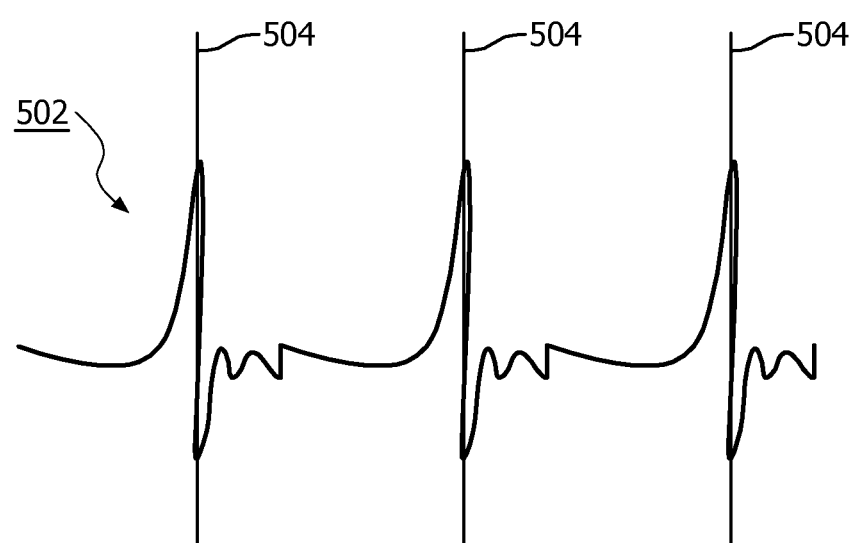
FIG. 5 is an electro-cardiogram (ECG) graph showing trigger points for measuring PPG signals in accordance with another embodiment.

Referring to FIG. 5, an electrocardiogram (ECG) graph 502 provides a waveform, which may be employed to trigger PPG signal measurements. This facilitates the collecting of PPG signals to validate or check, e.g., graft patency. Using the ECG signal, the endoscope is triggered at e.g., corresponding points 504 on the graph 502 to collect an image at exactly a same place/time in corresponding cycles during a heart cycle. This minimizes motion artifacts in the PPG signal. Other timing signals may also be employed, e.g., breathing cycles, etc.

Figure 6:
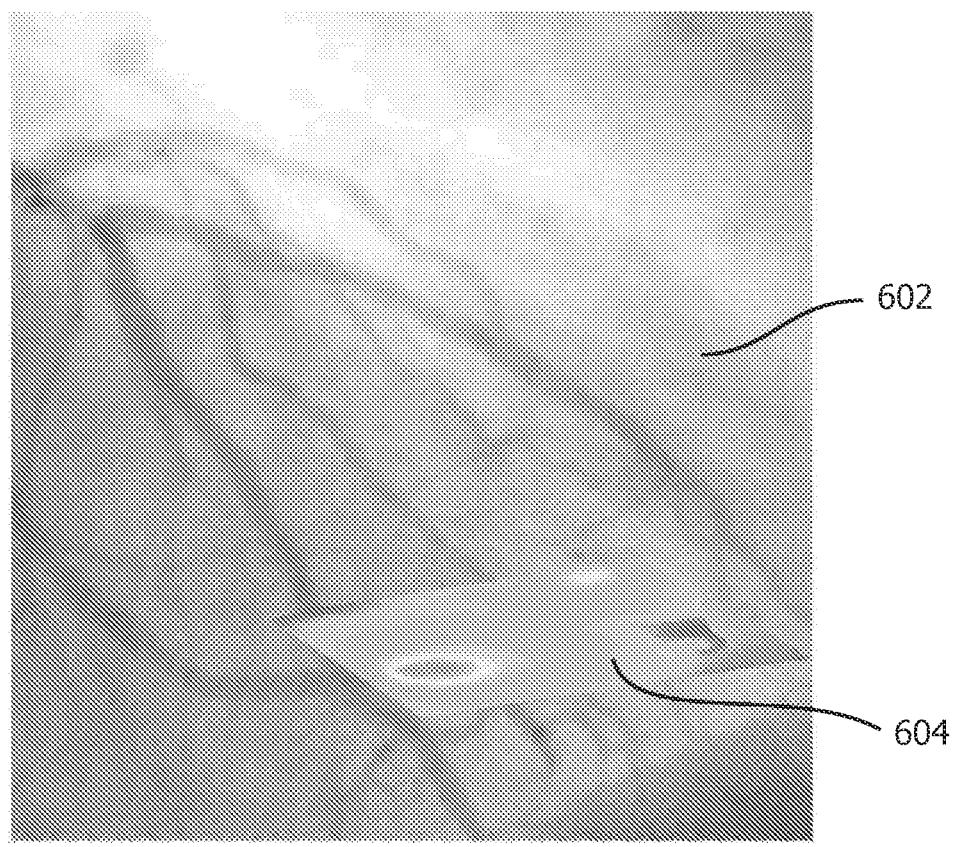
FIG. 6 is an X-ray image (angiogram) showing a heart with a PPG image/PPG map
Figure 7:
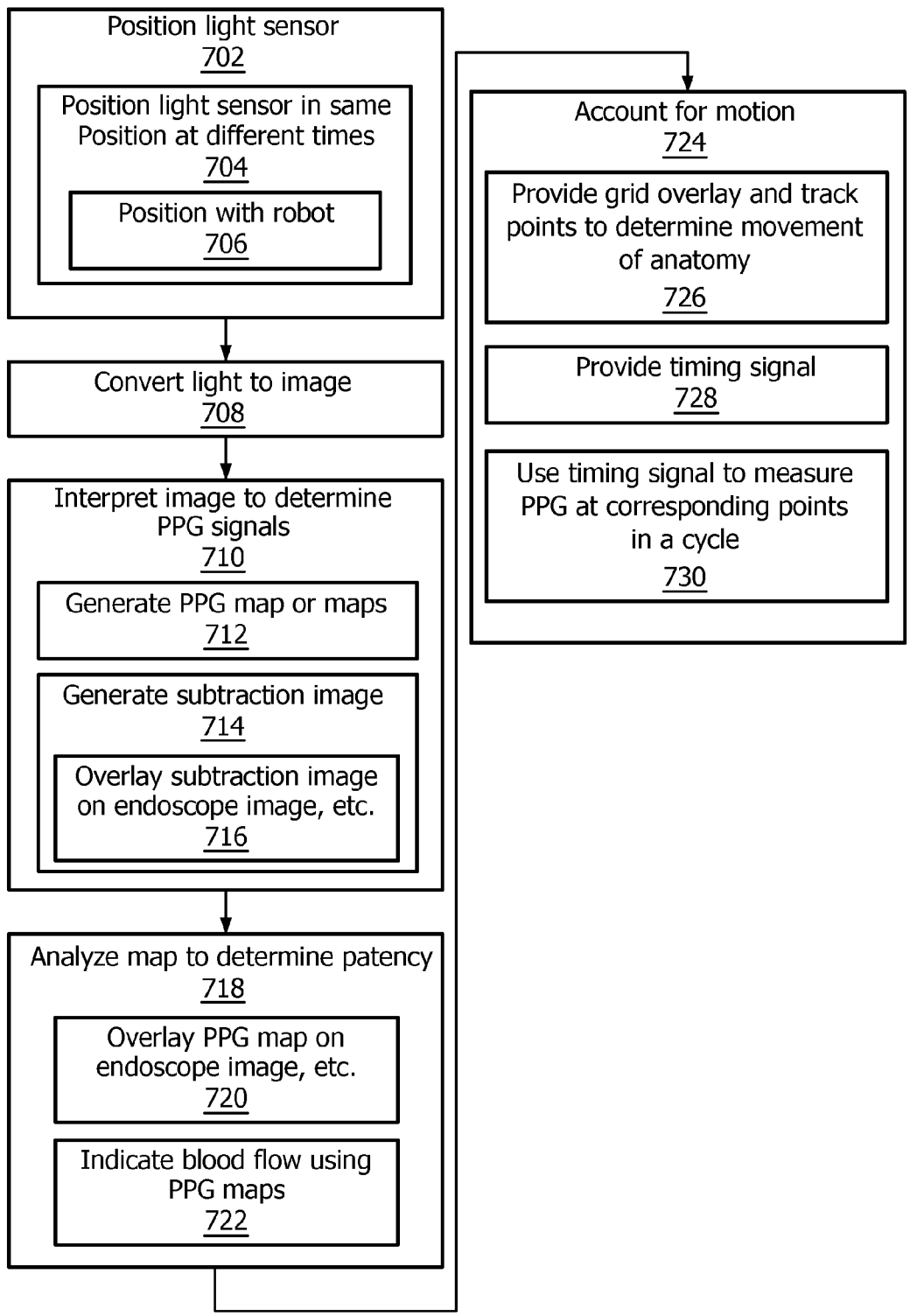
FIG. 7 is a flow diagram showing a method for patency evaluation in accordance with an illustrative embodiment.

Referring to FIG. 6, a graft or other anatomical feature may be checked by employing two or more imaging modalities. For example, a combination of X-ray graft patency and PPG graft patency validation may be performed. Coordinate frames of the X-ray images and the endoscopy images may be registered by known methods. Such methods can be extended to PPG imaging as these images are processed from the endoscope stream. In this way, an X-ray image 602 (e.g., a coronary angiogram) and a PPG image 604 can be combined to Referring to FIG. 7, a method for evaluating patency of a blood vessel or blood flow through tissue is illustratively shown in accordance with the present principles. In block 702, a light sensor is positioned relative to a blood vessel to receive light from the blood vessel. The light sensor may include a camera, and the camera may be mounted on one of an endoscope or over an open incision. In block 704, positioning the light sensor may include positioning the light sensor in a same position at different times such that PPG signals may be compared to determine PPG changes in the blood vessel. In another embodiment, a robot may be employed to permit repeatable positioning of the light sensor at different times in block 706.

In block 708, the light is converted into an image signal. In block 710, the image signal is interpreted to determine photo-plethysmography (PPG) signals and output pixel values in an image representing PPG information. In block 712, a PPG map is generated to be output to a display for analysis from the pixel values. In block 714, a subtraction image of the PPG signals generated at different times may be provided. In block 716, the subtraction image or PPG map may be overlaid on an image collected by the light sensor (e.g., over the endoscope image) or other image. It should be noted that other operations may be performed between the PPG maps to provide a comparison.

In block 718, at least one PPG map is analyzed to determine patency of the blood vessel. In block 720, the PPG map may be overlaid on an endoscope image, an X-ray image, an ultrasound image, etc. In block 722, the blood vessel may include a bypass graft, and the PPG map may indicate blood flow through the graft at different times.

In block 724, motion of the area of interest is accounted for. Two examples follow although other methods may be employed. In block 726, a grid overlay may be generated on the image signal of the blood vessel. Each portion of the grid may include a tracked point to is provided (e.g., an electrocardiogram (ECG) signal). In block 730, the timing signal is employed for triggering a PPG measurement at corresponding positions along the timing signal to account for motion of the blood vessel.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for evaluation of patency using photo-plethysmography on endoscope images (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for evaluating patency, comprising:
a light source configured to generate light for illuminating a blood vessel;
a light sensor positioned on an endoscope and positionable relative to the blood vessel, the light sensor being configured to receive light from the blood vessel responsive to the generated light and convert the light into an image signal;
a photo-plethysmography (PPG) interpretation module configured to receive the image signal and output pixel values in an image representing PPG information; and
an image generation module coupled to the PPG interpretation module and configured to receive the pixel values and generate a PPG map to be output to a display for analysis.

2. The system as recited in claim 1, wherein the light sensor includes a camera.

3. The system as recited in claim 1, further comprising a robot which includes the light sensor mounted thereon, the robot being configured to position the light sensor relative to the blood vessel.

4. The system as recited in claim 1, wherein the light sensor is configured to be positioned at a position relative to the blood vessel at a first time to obtain a first PPG map and is further configured to be positioned in the same position at a second time to obtain a second PPG map, enabling comparison of the first and second PPG map to determine PPG changes in the blood vessel.

5. The system as recited in claim 4, further comprising a robot which includes the light sensor mounted thereon, the robot being configured to enable repeatable positioning of the light sensor at different times.

6. The system as recited in claim 1, wherein the image generation module is further configured to generate a subtraction image of the first and second PPG maps from the first and second times.

7. The system as recited in claim 1, wherein the image generation module is further configured to overlay the subtraction image on an image from the image signal provided by the light sensor.

8. The system as recited in claim 1, wherein the image generation module is further configured to overlay the PPG map on an image from the image signal provided by the light sensor.

9. The system as recited in claim 1, wherein the image generation module is further configured to overlay the PPG map on an X-ray image.

10. The system as recited in claim 1, wherein the blood vessel includes a bypass graft and the PPG map indicates blood flow through the graft at different times.

11. The system as recited in claim 1, wherein the light source is positioned on the endoscope.

12. A method for evaluating patency, comprising:
positioning a light sensor relative to a blood vessel using an endoscope to receive light from the blood vessel illuminated by a radiation source;
converting the light received from the blood vessel into an image signal;
interpreting the image signal to determine a photo-plethysmography (PPG) signal and outputting pixel values in an image representing PPG information;
generating a PPG map to be output to a display for analysis from the pixel values; and
analyzing at least one PPG map to determine patency of the blood vessel.

13. The method as recited in claim 12, wherein the light sensor includes a camera mounted on endoscope.

14. The method as recited in claim 12, wherein positioning the light sensor includes positioning the light sensor at a same position at different times to enable determination of respective PPG signals, and comparing the PPG signals to determine PPG changes in the blood vessel, and wherein positioning the light sensor includes employing a robot having the light sensor mounted thereon and moving the robot to permit repeatable positioning of the light sensor at different times.

15. The method as recited in claim 12, further comprising accounting for motion in the blood vessel to register PPG maps, wherein the accounting includes providing a grid overlaid on the image signal of the blood vessel, wherein each portion of the grid includes a tracked point to follow to determine the motion of the blood vessel.

* * * * *